United States Patent
Read et al.

(10) Patent No.: US 11,534,572 B2
(45) Date of Patent: Dec. 27, 2022

(54) EARPHONES FOR MEASURING AND ENTRAINING RESPIRATION

(71) Applicant: Bose Corporation, Framingham, MA (US)

(72) Inventors: Jack Read, Bolton, MA (US); Tegan Ayers, Rochester, MA (US); Christopher R. Paetsch, Cambridge, MA (US); Harsh Anilkant Mankodi, Brighton, MA (US); Andrew D. Dominijanni, Newton, MA (US); Daniel M. Gauger, Jr., Berlin, MA (US); Romain Kirszenblat, Allston, MA (US); Lifun Lin, Lincoln, MA (US); Mikhail Ioffe, Newton, MA (US)

(73) Assignee: Bose Corporation, Framingham, MA (US)

( * ) Notice: Subject to any disclaimer, the term of this patent is extended or adjusted under 35 U.S.C. 154(b) by 310 days.

(21) Appl. No.: 16/865,626

(22) Filed: May 4, 2020

(65) Prior Publication Data
US 2020/0261691 A1    Aug. 20, 2020

Related U.S. Application Data

(62) Division of application No. 15/655,845, filed on Jul. 20, 2017, now Pat. No. 10,682,491.

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/0816* (2013.01); *A61B 5/6803* (2013.01);
(Continued)

(58) Field of Classification Search
CPC .......... A61M 21/02; A61M 2021/0027; A61M 2021/0083; A61M 2021/0088;
(Continued)

(56) References Cited

U.S. PATENT DOCUMENTS

| | | |
|---|---|---|
| 5,238,001 A | 8/1993 | Gallant et al. |
| 8,199,956 B2 | 6/2012 | Haartsen et al. |

(Continued)

FOREIGN PATENT DOCUMENTS

| | | |
|---|---|---|
| CN | 102293013 B | 9/2014 |
| CN | 105430546 | 3/2016 |

(Continued)

OTHER PUBLICATIONS

First Office Action from CN Application No. 201880048094.6 dated Jan. 6, 2022.

*Primary Examiner* — Sunita Reddy
(74) *Attorney, Agent, or Firm* — Bose Corporation

(57) ABSTRACT

An earphone includes a loudspeaker, a microphone, a housing supporting the loudspeaker and microphone, and ear tip surrounding the housing and configured to acoustically couple both the loudspeaker and the microphone to an ear canal of a user, and to acoustically close the entrance to the user's ear canal. A processor provides output audio signals to the loudspeaker, receives input audio signals from the microphone, extracts a rate of respiration from the input audio signals, adjusts the output audio signals based on the extracted rate of respiration, and provides the adjusted output audio signals to the loudspeaker.

4 Claims, 8 Drawing Sheets

(51) Int. Cl.
*A61B 5/08* (2006.01)
*H04R 1/10* (2006.01)
*H04R 3/04* (2006.01)
*A61M 21/00* (2006.01)

(52) U.S. Cl.
CPC .......... *A61B 5/6817* (2013.01); *A61B 5/7257* (2013.01); *H04R 1/1016* (2013.01); *H04R 1/1041* (2013.01); *H04R 1/1075* (2013.01); *H04R 1/1083* (2013.01); *H04R 3/04* (2013.01); *A61M 2021/0027* (2013.01); *A61M 2021/0083* (2013.01); *A61M 2021/0088* (2013.01); *A61M 2205/3375* (2013.01); *A61M 2205/50* (2013.01); *A61M 2210/0662* (2013.01); *A61M 2230/06* (2013.01); *A61M 2230/42* (2013.01)

(58) Field of Classification Search
CPC ...... A61M 2205/3375; A61M 2205/50; A61M 2210/0662; A61M 2230/06; A61M 2230/42; A61B 5/0816; A61B 5/6803; A61B 5/6817; A61B 5/7257; H04R 1/1016; H04R 1/1041; H04R 1/1075; H04R 1/1083; H04R 3/04
USPC ..................................... 600/26–28
See application file for complete search history.

(56) References Cited

U.S. PATENT DOCUMENTS

| | | | | |
|---|---|---|---|---|
| 9,635,452 | B2* | 4/2017 | Cheng | ................. H04R 1/1075 |
| 9,690,376 | B2 | 6/2017 | Davis et al. | |
| 2002/0091049 | A1* | 7/2002 | Hisano | .............. A63B 71/0686 |
| | | | | 482/148 |
| 2004/0077934 | A1* | 4/2004 | Massad | ..................... A63F 9/24 |
| | | | | 128/903 |
| 2007/0113649 | A1 | 5/2007 | Bharti et al. | |
| 2007/0118011 | A1* | 5/2007 | Harrison | ............... H04R 25/456 |
| | | | | 607/137 |
| 2008/0107287 | A1 | 5/2008 | Beard | |
| 2008/0146890 | A1* | 6/2008 | Le | ........................... A61B 5/031 |
| | | | | 600/300 |
| 2008/0171945 | A1* | 7/2008 | Dotter | .................... A61B 5/486 |
| | | | | 600/529 |
| 2009/0143636 | A1* | 6/2009 | Mullen | ................ A61B 5/4812 |
| | | | | 600/26 |
| 2010/0125218 | A1* | 5/2010 | Haartsen | ................ A61B 5/6817 |
| | | | | 600/528 |
| 2010/0240945 | A1* | 9/2010 | Bikko | .................... A61B 7/003 |
| | | | | 600/28 |
| 2011/0295083 | A1* | 12/2011 | Doelling | .................. A61B 5/11 |
| | | | | 600/407 |
| 2012/0225412 | A1* | 9/2012 | Wagner | .................. G16H 40/67 |
| | | | | 434/236 |
| 2013/0034258 | A1* | 2/2013 | Lin | ......................... A61F 11/08 |
| | | | | 381/380 |
| 2014/0141395 | A1* | 5/2014 | Gavish | .................. A61B 5/486 |
| | | | | 434/236 |
| 2015/0154950 | A1* | 6/2015 | Ring | ................ G10K 11/17881 |
| | | | | 381/71.6 |
| 2015/0351688 | A1* | 12/2015 | Just | ...................... A61B 5/6817 |
| | | | | 600/407 |
| 2016/0151603 | A1 | 6/2016 | Shouldice et al. | |
| 2017/0195811 | A1 | 7/2017 | Ten et al. | |
| 2017/0258329 | A1* | 9/2017 | Marsh | ....................... G01J 5/12 |
| 2018/0014741 | A1 | 1/2018 | Chou | |
| 2019/0022348 | A1 | 1/2019 | Read et al. | |
| 2019/0231197 | A1 | 8/2019 | Kirszenblat et al. | |
| 2019/0231198 | A1 | 8/2019 | Hirota et al. | |
| 2019/0239772 | A1 | 8/2019 | Grace et al. | |

FOREIGN PATENT DOCUMENTS

| | | |
|---|---|---|
| CN | 105027030 A | 10/2018 |
| FR | 2758709 B1 | 2/1999 |

* cited by examiner

EARPHONES FOR MEASURING AND ENTRAINING RESPIRATION

RELATED APPLICATIONS

This application is a division of U.S. patent application Ser. No. 15/655,845, filed Jul. 20, 2017, which is related to, and incorporates by reference, U.S. patent application Ser. No. 15/106,989, filed Jun. 21, 2016; application Ser. No. 15/348,400, filed Nov. 10, 2016; and application Ser. No. 15/352,034, filed Nov. 17, 2016, all titled Intelligent Earplug System. It is also related to U.S. patent application Ser. No. 15/267,567, entitled Sleep Assistance Device; application Ser. No. 15/267,464, entitled Sleep Quality Scoring and Improvement; application Ser. No. 15/267,552, entitled Intelligent Wake-Up System; application Ser. No. 15/267,848, entitled Sleep System; application Ser. No. 15/267,858, entitled User Interface for a Sleep System; and application Ser. No. 15/267,886, entitled Sleep Assessment Using a Home Sleep System, all of which were filed on Sep. 16, 2016. This application is also related to U.S. patent application Ser. No. 15/655,863, titled Sleep Assistance Device For Multiple Users, filed Jul. 20, 2017, which is incorporated here by reference.

BACKGROUND

This disclosure relates to earphones for measuring and entraining respiration.

Sleeplessness and poor or interrupted sleep may significantly affect a person's health. Poor sleep may be caused by such factors as ambient noise, stress, medical conditions, or discomfort. Thus, there exists a need for a sleep aid that can help address the underlying causes of poor sleep without adversely affecting the user's health in other, unintended ways.

SUMMARY

In general, in one aspect, a system includes an earphone, which includes a loudspeaker, a microphone, a housing supporting the loudspeaker and microphone, and ear tip surrounding the housing and configured to acoustically couple both the loudspeaker and the microphone to an ear canal of a user, and to acoustically close the entrance to the user's ear canal. A processor provides output audio signals to the loudspeaker, receives input audio signals from the microphone, extracts a rate of respiration from the input audio signals, adjusts the output audio signals based on the extracted rate of respiration, and provides the adjusted output audio signals to the loudspeaker.

Implementations may include one or more of the following, in any combination. Adjusting the output audio signals may include adjusting a rhythm of the output audio signals to be about one cycle per minute less than the detected respiration rate. Adjusting the output audio signals may include transitioning the output audio signals from respiration entrainment sounds to masking sounds. Adjusting the output audio signals may include transitioning the output audio signals from masking sounds to awakening sounds. The earphone may include a memory storing sound files, and providing the output audio signals may include retrieving a first sound file from the memory. Adjusting the output audio signals may include retrieving a second sound file from the memory and using the second sound file to generate the output audio signal. The processor may be integrated within the earphone. The processor may be integrated within a portable computing device.

The processor may extract the rate of respiration by detecting peaks having a frequency of around 1 Hz in the input audio signals, based on the detected peaks, computing an instantaneous heart rate, measuring a frequency of an oscillation within the instantaneous heart rate, and based on the frequency of the oscillation, computing the rate of respiration. The processor may measure the frequency of the oscillation within the instantaneous heart rate by computing a fast Fourier transform (FFT) of the instantaneous heart rate. The processor may measure the frequency of the oscillation within the instantaneous heart rate by computing a gradient of the instantaneous heart rate, and computing a fast Fourier transform (FFT) of the gradient of the instantaneous heart rate. The processor may measure the frequency of the oscillation within the instantaneous heart rate by detecting peaks of the instantaneous heart rate. The processor may measure the frequency of the oscillation within the instantaneous heart rate by fitting a sine function to the instantaneous heart rate, the frequency of the sine curve being the frequency of the oscillation. The system may include a second earphone including a second loudspeaker, a second microphone, a second housing supporting the second loudspeaker and second microphone, and a second ear tip surrounding the second housing and configured to acoustically couple both the second loudspeaker and the second microphone to a second ear canal of the user, and to acoustically close the entrance to the user's second ear canal, in which case the processor receives second input audio signals from the microphone, and detects the peaks having a frequency of around 1 Hz by combining the input audio signals from the first microphone with the second input audio signals, and detecting peaks within the result of the combination. Combining the input audio signals may include multiplying the amplitude of the first input audio signals by the amplitude of the second input audio signal, at each time that the two signals are sampled.

Providing the output audio signals to the loudspeaker may include providing signals which represent sounds across a first frequency band, the audio signals including a notch in which the sounds lack energy within a second frequency band narrower than the first frequency band, and the processor may be configured to extract the rate of respiration by applying a band-pass filter to the input audio signals to limit the input audio signals to a third frequency band contained within the second frequency band, and demodulating the filtered input audio signals to compute a rate of respiration corresponding to energy in the input audio signals in the third frequency band. The third frequency band may be coextensive with the second frequency band. The first frequency band may extend at least 40 Hz below a lower end of the second frequency band. The second frequency band may extend between about 250 to 350 Hz. The earphone may include a memory storing sound files, and providing the output audio signals may include retrieving a first sound file from the memory, the first sound file representing audio signals corresponding to sounds having energy in the second frequency band, and providing the output audio signals includes applying a notch filter to audio signals generated from the first sound file, to remove energy from the signals within the second frequency band. The first sound file may represent audio signals corresponding to sounds lacking energy in the second frequency band.

Advantages include acoustically sensing the respiration rate at the ear without interference from audio signals being generated by the earphone.

All examples and features mentioned above can be combined in any technically possible way. Other features and advantages will be apparent from the description and the claims.

DESCRIPTION

Several of the above-referenced applications describe a bedside system that detects a user's respiration rate and uses that to infer and manage their sleep state. In particular, to assist the user with falling asleep, the system plays sounds that have a rhythm slightly slower than the user's own respiration rate. This naturally leads the user to slow their breathing to match the rhythm of the sounds, in a process referred to as entrainment. As the user slows their rate of respiration, the rate of the sounds is further reduced, in a feedback loop that leads the user gradually to sleep. Once the user falls asleep (as indicated by artifacts in their respiration rate), the system switches to playing masking sounds, which diminish the user's ability to detect, and be disturbed by, external sounds. If the user is detected to be waking up too early, entrainment may be reactivated. When it is time for the user to wake up, the system may coordinate wake-up sounds with the user's sleep state and other information to wake the user in the least-disruptive way possible.

Others of the above-referenced applications describe intelligent earplugs which the user can wear while sleeping, and which provide masking sounds through the night, and alarm or alert sounds when needed. These earplugs are controlled by a smartphone, but principally operate autonomously, playing stored masking sounds until instructed otherwise by the controlling phone, or based on an internal clock. It would be advantageous if the intelligent earplugs could play the respiration-entraining sounds of the bedside systems, to help the user fall asleep without disturbing others who may be sharing the bed or room. One solution to that, described in U.S. application Ser. No. 15/655,836, now U.S. Pat. No. 10,478,590, is for the sleep system to inform the earplugs of the user's respiration rate and sleep state, and for the earplugs to adjust the rate of a rhythmic component in stored entrainment sounds as in the out-loud system.

This disclosure describes how to add respiration sensing to the earplugs themselves, so that the external system is not required, and the earplugs can operate fully autonomously, or with only a smart phone to control them.

Figure 1:
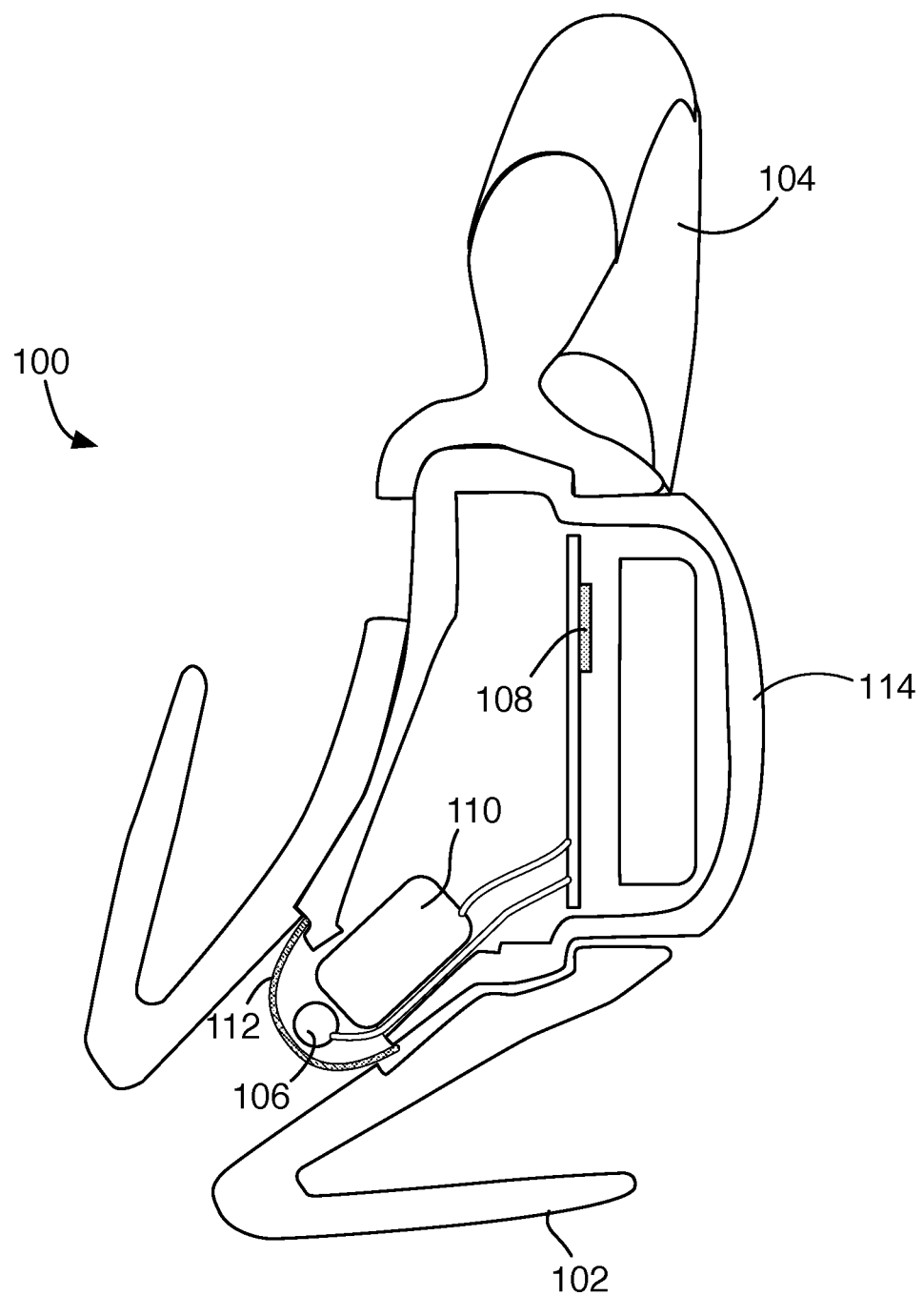
FIGS. 1 and 2 show cross-sectional views of earphones with an integrated microphones.
Figure 2:
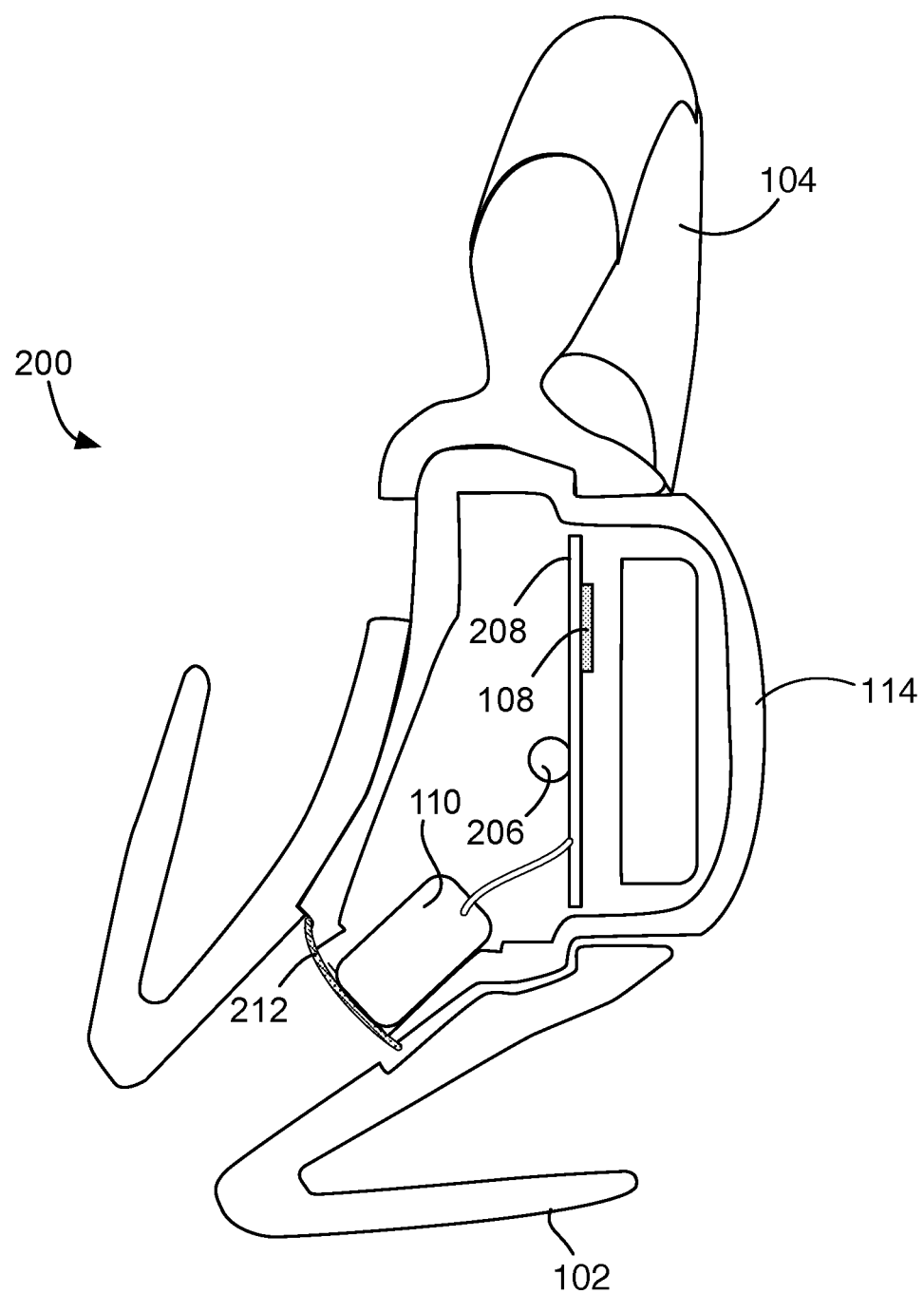
Figure 3:
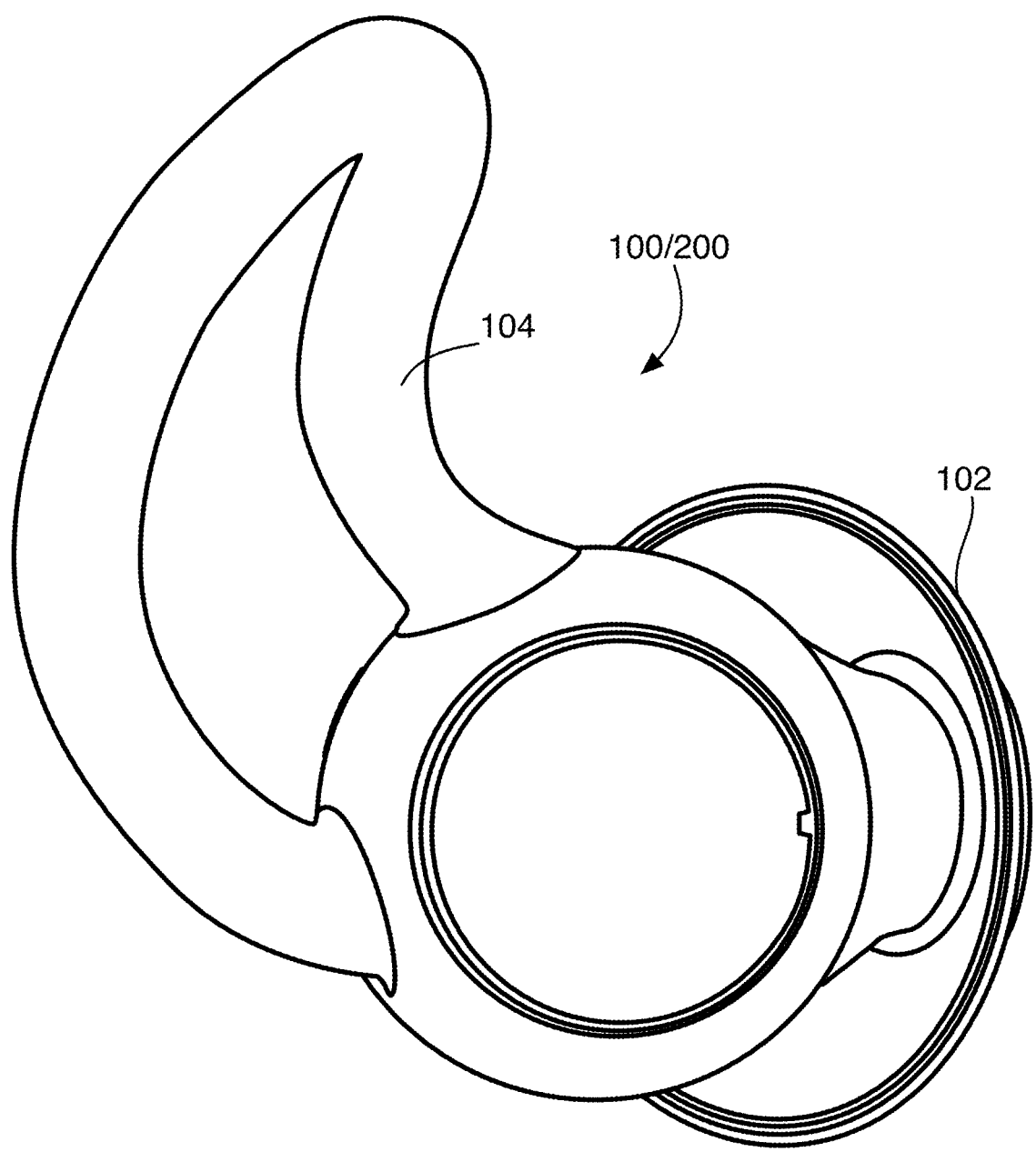
FIG. 3 shows an external view of the system of FIG. 1 or 2.

As shown in FIGS. 1, 2 and 3, sleep-sensing earphones 100 or 200 include an ear tip sealing structure 102 that blocks, or occludes, the entrance to the ear canal. FIGS. 1 and 2 show cross-sections of two different earphone examples, while FIG. 3 shows an exterior view, which is the same for the examples of either FIG. 1 or 2, for reference. A retaining structure 104 helps retain the earphone in the ear, and puts pressure on the sealing structure 102 to maintain the seal by pushing on the concha, opposite to where the sealing structure meets the ear canal. The sealing structure 102 helps to passively block outside sounds from entering the ear, increasing the effectiveness of the masking sounds played by the earphones.

Another result of occluding the ear canal is that sounds produced by the body, such as the heartbeat and respiration sounds, are amplified within the ear canal. With the addition of a microphone 106 (FIG. 1) or 206 (FIG. 2), the heartbeat can be sensed and its rate determined. The processor 108 on-board each earphone (or in one, if they coordinate their action) can then extract the respiration rate from the heartbeat signal, and adjust the timing of entrainment sounds being played to the user through a speaker 110. In the example of FIG. 1, the microphone 106 and speaker 110 are shown behind a screen 112, as described in U.S. Pat. No. 9,635,452, which is incorporated here by reference. The microphone may be mounted near or on the speaker 110, or integrated into the speaker housing 114. In the example of FIG. 2, the microphone 206 is mounted directly to the PCB 208 and the screen 212 is flat, or may not be needed; the volume inside the earbud is coupled to the ear canal via space around the speaker 110. As long as the earbud/ear canal system is effectively sealed at the frequencies of interest, the microphone will detect the targeted sounds coming from inside the ear canal. Other configurations that couple the microphone acoustically to the ear canal will also work.

Figure 4:
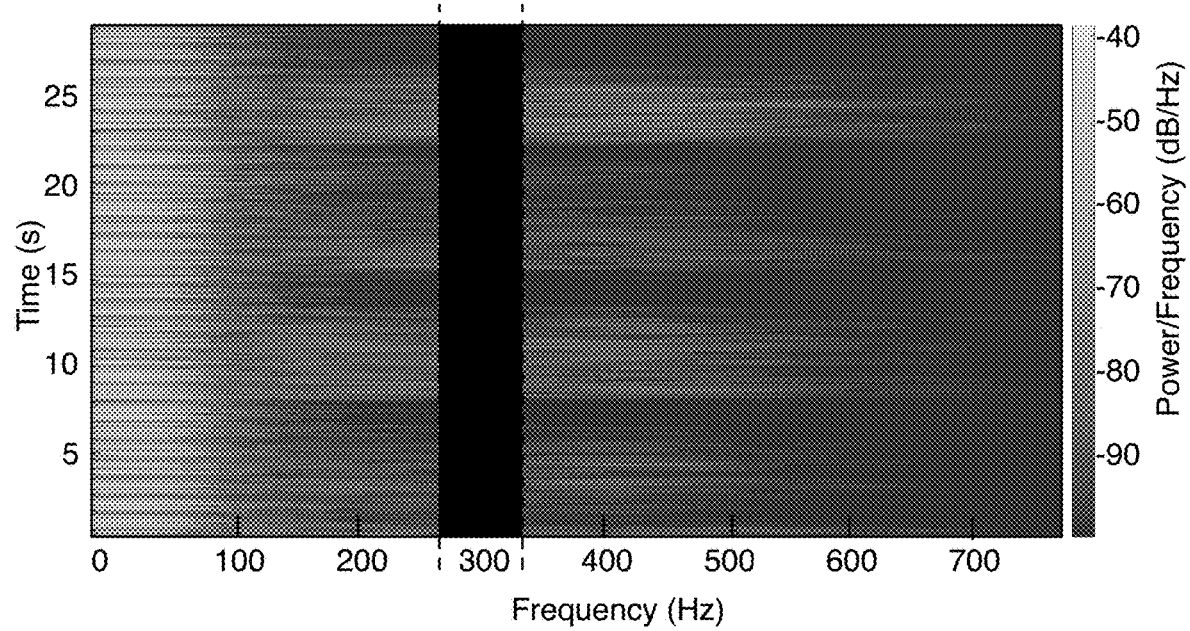
FIGS. 4, 5a, 5b, and 5c show audio spectrographs.
Figure 5A:
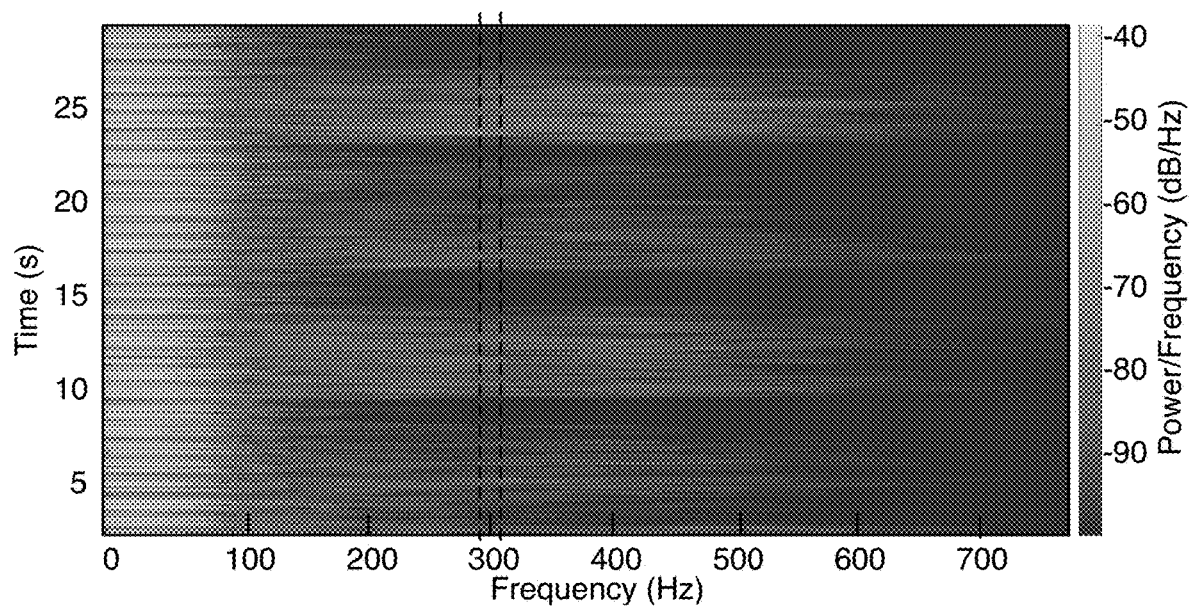
Figure 5B:
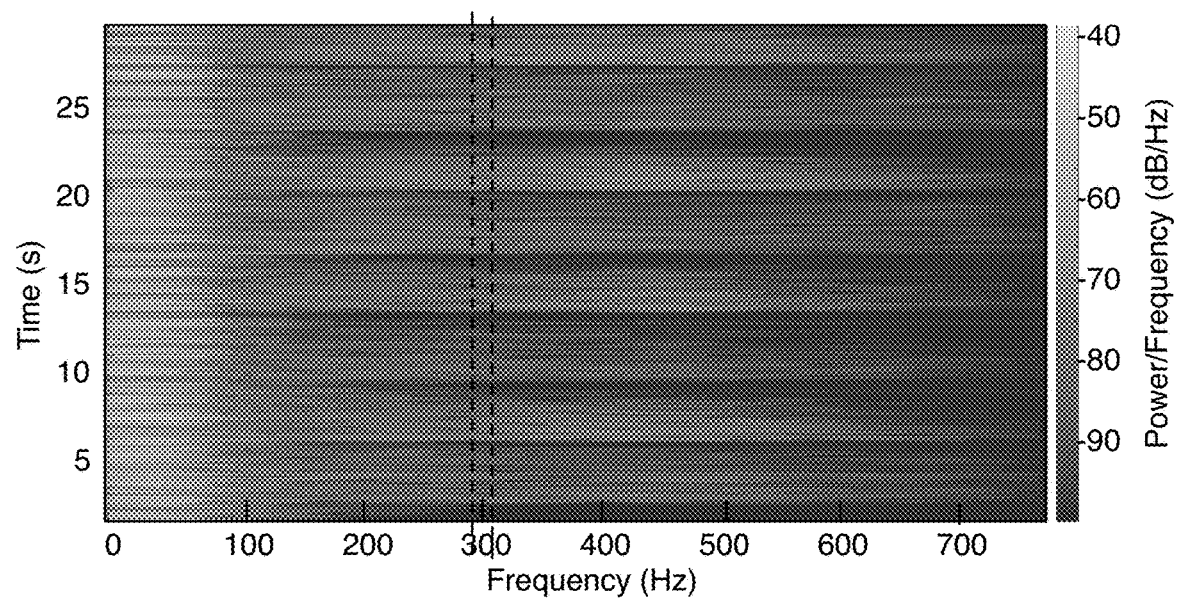
Figure 5C:
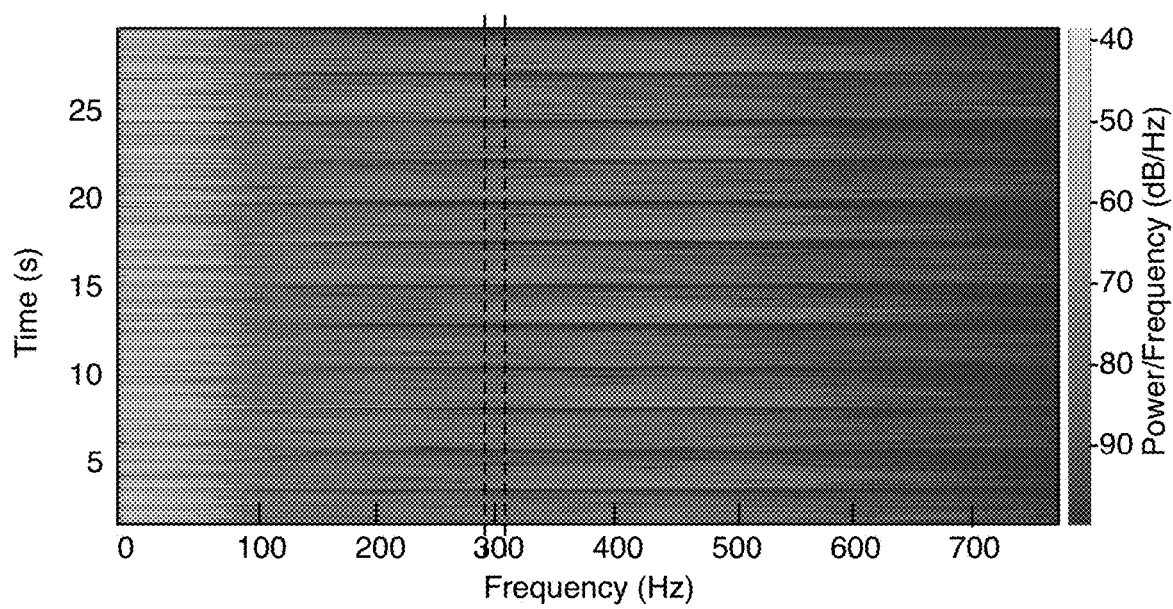

A difficulty arises in attempting to use a microphone coupled to the ear canal to detect respiration while the earphones are simultaneously playing sounds (and in particular, sounds which may not be significantly different from the sound of breathing). One solution, as shown in FIG. 4, is to notch out a small frequency band of the entrainment or masking sound, and to filter the microphone signal, shown in FIGS. 5a-5c for different respiration rates, with a corresponding band-pass filter. Due to the psychoacoustic phenomenon known as the upward spread of frequency, a user will not be able to audibly detect the small notch in the entrainment or masking sound, but enough of the sound of their respiration will be detectable within the notched and filtered window to measure their respiration rate.

Figure 6:
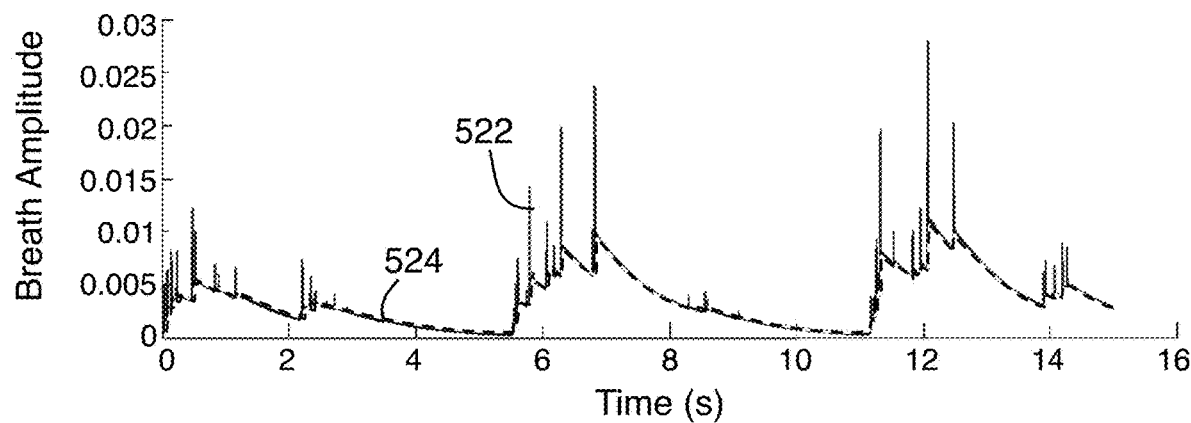
FIGS. 6 and 7 show graphs of data derived from the type of data shown in FIGS. 5a-5c.
Figure 7:
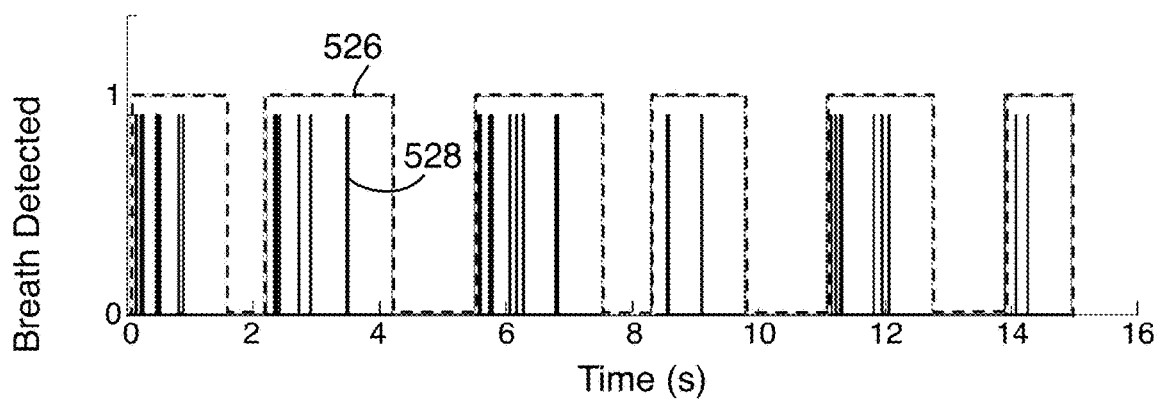

In particular, a notch in a range around 250-350 Hz will leave enough energy below the notch for the upper spread of frequency to hide the notch from the user. More specifically, a notch between 260-340 Hz has been found to be sufficient. The notch can either be removed from the masking or entrainment sound by a DSP during operation of the earplugs, or the stored sounds can simply have the notch already present A band-pass filter matching, or narrower than, the notch band is then applied to the microphone signal (dashed lines 502, 504 in FIGS. 5a-5c), which can be visualized as energy over time, as shown by the solid line 522 in FIG. 6. The respiration envelope is fit to the data, dashed line 524. A peak detection algorithm is applied, as shown in FIG. 7, to detect the respiration of the user, the rate of the clusters 526 of peaks 528 corresponding to breaths per minute.

The human heartbeat is infrasonic, while acoustic signatures from respiration can be observed in the 100s of Hz, so the heartbeat will be too low-frequency (and the high-frequency part of the heartbeat impulse too low-energy) to interfere with detection of respiration in the notched band. The heartbeat could also be removed from the microphone signal using an additional heart rate sensor, such as a photo-plethysmograph (PPG) sensor included in the earphones.

Alternatively, the heartbeat itself can be derived from the microphone signals, and the respiration rate can be extracted from the heart rate variability. Specifically, as shown in FIG. 6, the microphone coupled to the occluded ear canal detects heartbeats as energy peaks in a signal with a frequency of around 8-10 Hz (the heart rate itself is around 1 Hz). As this rate is far below the frequency range of the masking sounds, those sounds will not interfere with detecting the heartbeat. If both ears are equipped with microphones, and the signals are transmitted to the smart phone (or from one ear to the other) for analysis, combining the amplitudes of the two signals at each time sample, such as by multiplication, can greatly increase the signal to noise ratio, as shown in FIG. 7. Applying a peak-finding algorithm to the microphone signal and observing the distance between consecutive peaks yields the beat-to-beat or instantaneous, heart rate value, shown in FIG. 8.

Figure 8:
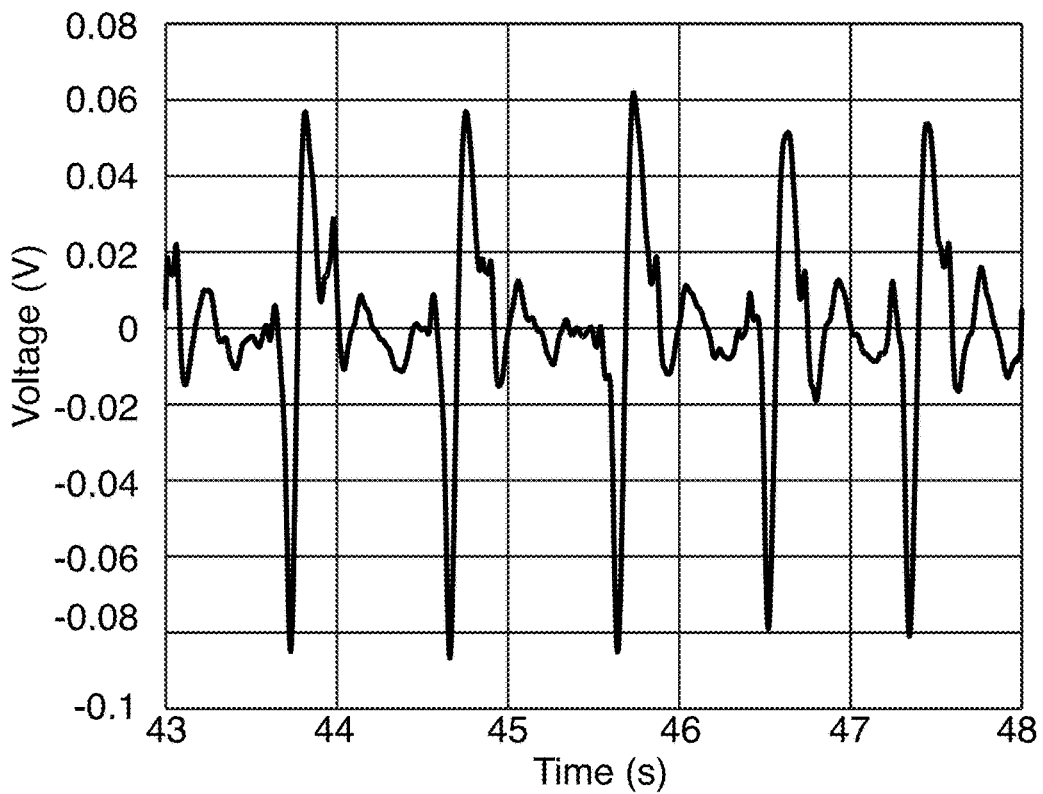
FIGS. 8-10 show graphs of sensor readings
Figure 9:
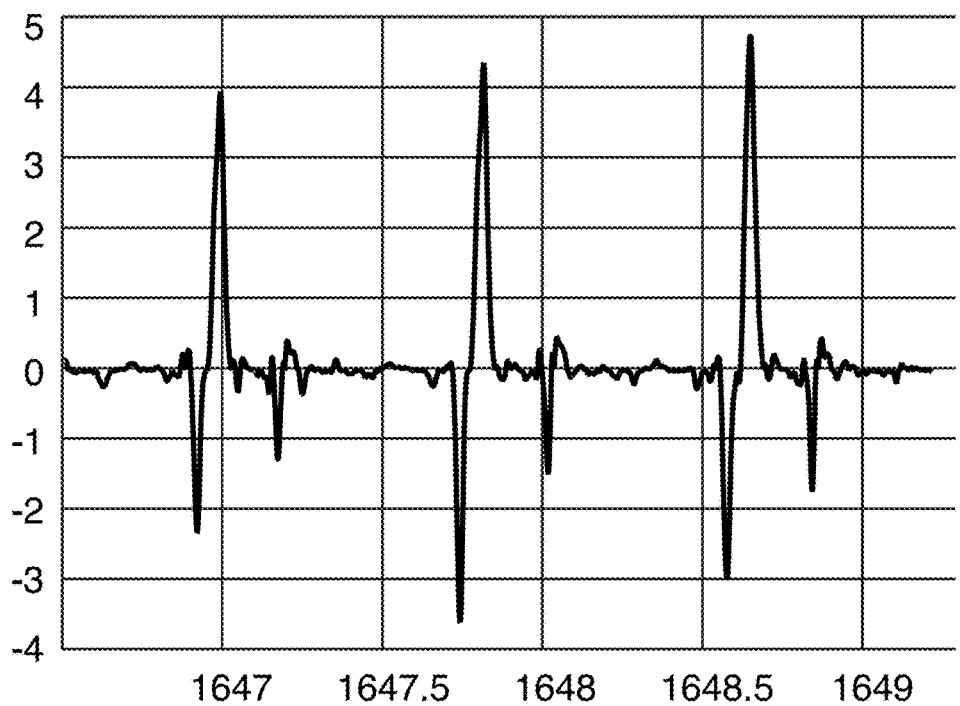
Figure 10:
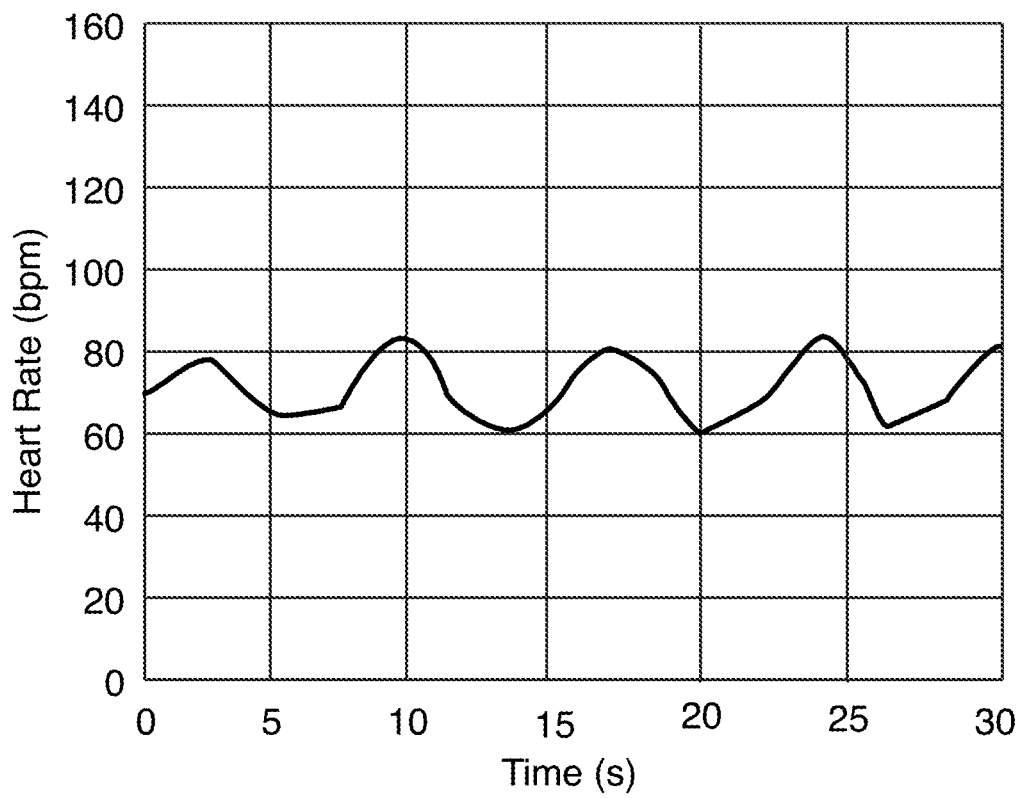

FIG. 8 shows that there is a cyclic variability to the instantaneous heart rate. The period of this variability happens to be the respiration rate—as the user inhales, their heart rate increases, and as they exhale, their heart rate decreases. Applying another peak detection step, or other frequency analysis such as a fast Fourier transform (FFT) or fitting a sine function to the curve, to the instantaneous heart rate or to its gradient reveals the respiration rate.

If the earphones happen to include a feedback-based active noise reduction (ANR) system, to further block environmental sounds, the system microphone of the ANR system would be more than adequate for detecting the sound of respiration or blood flow and measuring the respiration or heart rate, but it would be done within the feedback loop, so notching the anti-noise output of the ANR system would not be necessary. However, an ANR system is likely to consume a lot of power, and may not be suitable or necessary for sleep-focused earphones. Since the respiration or heart rate sensing is very narrow-band, a simpler MEMS microphone should be sufficient and a much lower-power component may be used, benefiting the overall battery life and component size of the earphones. Similarly, it may be possible to use an external device, such as a smartphone, to filter and demodulate the microphone signals to detect the respiration rate or heart rate, and to modify the output sounds accordingly, but battery life may be better served by doing all the processing within the earphones. The trade-off between power for processing and power for communication may depend on factors unrelated to the acoustics, including battery size, antenna placement, and memory requirements, to name a few.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, hard disks, optical disks, solid-state disks, flash ROMS, nonvolatile ROM, and RAM. Furthermore, it should be understood by one of skill in the art that the computer-executable instructions may be executed on a variety of processors such as, for example, microprocessors, digital signal processors, and gate arrays.

For ease of exposition, not every step or element of the systems and methods described above is described herein as part of a computer system, but those skilled in the art will recognize that each step or element may have a corresponding computer system or software component. Such computer system and software components are therefore enabled by describing their corresponding steps or elements (that is, their functionality), and are within the scope of the disclosure.

A number of implementations have been described. Nevertheless, it will be understood that additional modifications may be made without departing from the scope of the inventive concepts described herein, and, accordingly, other embodiments are within the scope of the following claims.

What is claimed is:

1. A method of adjusting sounds heard by a user of an earphone, the method comprising:
providing output audio signals to a loudspeaker supported by a housing and acoustically coupled to the user's ear canal by an ear tip surrounding the housing and acoustically closing the entrance to the user's ear canal;
receiving input audio signals from a microphone in the housing and also acoustically coupled to the user's ear canal by the ear tip; and
in a processor
extracting a rate of respiration from the input audio signals;
adjusting the output audio signals based on the extracted rate of respiration; and
providing the adjusted output audio signals to the loudspeaker,
wherein:
the step of providing the output audio signals to the loudspeaker comprises providing signals which represent sounds across a first frequency band, the audio signals including a notch in which the sounds lack energy within a second frequency band narrower than the first frequency band; and
the processor is configured to extract the rate of respiration by
applying a band-pass filter to the input audio signals to limit the input audio signals to a third frequency band contained within the second frequency band; and
demodulating the filtered input audio signals to compute the rate of respiration corresponding to energy in the input audio signals in the third frequency band.

2. The method of claim 1, wherein the step of adjusting the output audio signals comprises adjusting a rhythm of the output audio signals to be about one cycle per minute less than the extracted rate of respiration.

3. The method of claim 1, wherein the step of adjusting the output audio signals comprises transitioning the output audio signals from respiration entrainment sounds to masking sounds.

4. The method of claim 1, wherein the step of adjusting the output audio signals comprises transitioning the output audio signals from masking sounds to awakening sounds.

* * * * *